US009663487B2

(12) United States Patent
Shuttleworth et al.

(10) Patent No.: US 9,663,487 B2
(45) Date of Patent: May 30, 2017

(54) PHOSPHOINOSITIDE 3-KINASE INHIBITORS

(71) Applicant: Karus Therapeutics Limited, Abingdon, Oxfordshire (GB)

(72) Inventors: Stephen Joseph Shuttleworth, Oxfordshire (GB); Franck Alexandre Silva, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 14/382,196

(22) PCT Filed: Mar. 8, 2013

(86) PCT No.: PCT/GB2013/050583
§ 371 (c)(1),
(2) Date: Aug. 29, 2014

(87) PCT Pub. No.: WO2013/132270
PCT Pub. Date: Sep. 12, 2013

(65) Prior Publication Data
US 2015/0080395 A1 Mar. 19, 2015

(30) Foreign Application Priority Data
Mar. 8, 2012 (GB) .................................. 1204125.7

(51) Int. Cl.
*C07D 401/04* (2006.01)
*C07D 413/14* (2006.01)

(52) U.S. Cl.
CPC ......... *C07D 401/04* (2013.01); *C07D 413/14* (2013.01)

(58) Field of Classification Search
CPC .......................... C07D 401/04; C07D 413/14
See application file for complete search history.

(56) References Cited

U.S. PATENT DOCUMENTS

| 3,491,092 | A | 1/1970 | Grigat et al. |
| 4,017,500 | A | 4/1977 | Mayer et al. |
| 5,703,075 | A | 12/1997 | Gammill et al. |
| 7,361,662 | B2 | 4/2008 | Rault et al. |
| 8,981,087 | B2 | 3/2015 | Shuttleworth et al. |
| 9,200,007 | B2 | 12/2015 | Shuttleworth et al. |
| 9,266,879 | B2 | 2/2016 | Shuttleworth et al. |
| 2002/0151544 | A1 | 10/2002 | Hayakawa et al. |
| 2007/0135466 | A1* | 6/2007 | Ledeboer ............. C07D 487/04 514/275 |
| 2011/0201608 | A1 | 8/2011 | Hoffmann et al. |
| 2013/0109688 | A1 | 5/2013 | Shuttleworth et al. |
| 2015/0080395 | A1 | 3/2015 | Shuttleworth et al. |
| 2016/0108057 | A1 | 4/2016 | Shuttleworth et al. |
| 2016/0347771 | A1 | 12/2016 | Shuttleworth et al. |

FOREIGN PATENT DOCUMENTS

| EP | 1277738 A1 | 1/2003 |
| EP | 1724267 A1 | 11/2006 |
| WO | WO-01/83456 A1 | 11/2001 |
| WO | WO 02/02551 A1 | 1/2002 |
| WO | WO-02/085400 A1 | 10/2002 |
| WO | WO-2004/006846 A2 | 1/2004 |
| WO | WO-2004/043956 A1 | 5/2004 |
| WO | WO-2006/046035 A1 | 5/2006 |
| WO | WO-2006/127587 A1 | 11/2006 |
| WO | WO 2006/127587 A1 | 11/2006 |
| WO | WO 2007/084667 A2 | 7/2007 |
| WO | WO-2007/122410 A1 | 11/2007 |
| WO | WO-2007/127183 A1 | 11/2007 |
| WO | WO-2008/064018 A1 | 5/2008 |
| WO | WO 2008/094992 A2 | 8/2008 |
| WO | WO-2008/121257 A1 | 10/2008 |
| WO | WO 2008/145688 A2 | 12/2008 |
| WO | WO-2008/150827 A1 | 12/2008 |
| WO | WO-2010/015520 A1 | 2/2010 |
| WO | WO-2010/037765 A2 | 4/2010 |

(Continued)

OTHER PUBLICATIONS

Somei et al., Chem. Pharm. Bull. 34(9), 3971-3973, (1986).*
Alvarez-Rua et al., "Multiple Hydrogen Bonds and Tautomerism in Naphthyridine Derivatives", New J. Chem. 28, 700-07 (2004).
Baldev Singh et al., "Novel cAMP PDE III Inhibitors: 1,6-Naphthyridin-2(18)-ones", Journal of Medicinal Chemistry, American Chemical Society, 35(26): 5858-4865, Jan. 1, 1992, New York.
CAS Registry Nos. 1214438-02-4 and 1214393-37-9 (Mar. 25, 2010).
D.A. Kovalskiy et al., "Synthesis of 7-(3-piperidyl)[1,6]naphthyridine and 7-(4-piperidyl)[1,6]naphthyridine", Chemistry of Heterocyclic Compounds, 45(9): 1053-1057, Nov. 24, 2009.
Database Chemcats [Online], Chemical Abstracts Service, Apr. 22, 2011, Columbus, Ohio.
Erik L. Meredith et al., "Identification of Orally Available Naphthyridine Protein Kinase D Inhibitors", Journal of Medicinal Chemistry, 53(15): 5400-5421, Aug. 12, 2010.

(Continued)

*Primary Examiner* — Rebecca Anderson
(74) *Attorney, Agent, or Firm* — Goodwin Procter LLP

(57) ABSTRACT

A compound of formula I: or a pharmaceutically acceptable salt thereof, wherein: $R_1$, $R_2$, $R_3$, R and $R_6$ are each independently $(LQ)_m Y$; $R_4$ is H, halogen, optionally substituted aryl or optionally substituted alkyl; and; each X is independently $CR_7$ or N. The compounds are PI3K inhibitors and therefore have potential utility in therapy.

15 Claims, No Drawings

(56) References Cited

FOREIGN PATENT DOCUMENTS

| WO | WO-2010/052569 A2 | 5/2010 |
|---|---|---|
| WO | WO-2011/012883 A1 | 2/2011 |
| WO | WO-2011/021038 A1 | 2/2011 |
| WO | WO-2011/079231 A1 | 6/2011 |
| WO | WO-2011/135351 A1 | 11/2011 |
| WO | WO-2013/014448 A1 | 1/2013 |
| WO | WO-2013/017480 A1 | 2/2013 |
| WO | WO-2013/132270 A1 | 9/2013 |
| WO | WO-2014/081718 A1 | 5/2014 |
| WO | WO-2014/181137 A1 | 11/2014 |
| WO | WO-2014/210354 A1 | 12/2014 |
| WO | WO-2015/054355 A1 | 4/2015 |
| WO | WO-2015/121657 A1 | 8/2015 |

OTHER PUBLICATIONS

Hayakawa, et al., "Synthesis and Biological Evaluation of Pyrido[3',2':4,5]furo[3,2-d]pyrimidine Derivatives as Novel PI3 Kinase p110α Inhibitors" Bioorganic & Medicinal Chemistry Letters, 2007, vol. 17, pp. 2438-2442.
International Preliminary Report on Patentability and Written Opinion of the International Searching Authority for PCT/GB2010/051221 dated Jan. 31, 2012 (7 pages).
International Preliminary Report on Patentability and Written Opinion of the International Searching Authority for PCT/GB2010/051370 dated Feb. 21, 2012 (6 pages).
International Preliminary Report on Patentability and Written Opinion of the International Searching Authority for PCT/GB2011/050824 dated Nov. 6, 2012 (7 pages).
International Preliminary Report on Patentability and Written Opinion of the International Searching Authority for PCT/GB2013/050583 dated Sep. 9, 2014 (6 pages).
International Search Report of the International Searching Authority for PCT/GB2010/051221 dated Oct. 7, 2010 (4 pages).
International Search Report of the International Searching Authority for PCT/GB2010/051370 dated Nov. 9, 2010 (4 pages).
International Search Report of the International Searching Authority for PCT/GB2011/050824 dated Jul. 12, 2011 (5 pages).
International Search Report of the International Searching Authority for PCT/GB2013/050583 dated May 6, 2013 (4 pages).
Saifuddin, Mohammad et al. "Water-Accelerated Cationic π-(7-endo) Cyclisation: Application to Indole-Based Peri-Annulated Polyheterocycles," *European Journal of Organic Chemistry*, 2010, 2010(26):5108-5117.
U.S. Appl. No. 15/000,543, Naphthridine Derivatives as PI3K Inhibitors for the Treatment of Cancer and Immune-Inflammatory Disease, filed Jan. 19, 2016.
Ameriks et al., "Small Molecule Inhibitors of Phosphoinositide 3-Kinase (PI3K) δ and γ", Current Topics in Medicinal Chemistry, 2009, vol. 9, No. 8, pp. 738-753.
Cohen et al., Current Opinion in Chemical Biology, 3, 459-465, 1999.
Fabbro et al. Pharmacology & therapeutics 93, 79-98, 2002.
Golub et al., Science, 286, 531-537, 1999.
Hollebecque A et al., (2014), 'A Phase 1b Trial of LY2584702 Tosylate, a p70 S6 Inhibitor, in Combination with Erlotinib or Everolimus in Patients with Solid Tumours,' Eur J Cancer, 50(5):876-84.

International Preliminary Report on Patentability and Written Opinion of the International Searching Authority for PCT/GB2015/050396 dated Aug. 16, 2016 (6 pages).
Zhou W et al., (2009) Novel Mutant-Selective EGFR Kinase Inhibitors Against EGFR T790M, Nature, 462(7276):1070-4 [NIH Public Access Version].
International Search Report of the International Searching Authority for PCT/GB2015/050396 mailed Mar. 25, 2015 (3 pages).
Lin L et al., (2014), 'Dual Targeting of Glioblastoma Multiforme with a Proteasome Inhibitor (Velcade) and a Phosphatidylinositol 3-Kinase Inhibitor (ZSTK474),' Int J Oncol, 44(2):557-62.
Mass, R. D., Int. J. Radiation Oncology Bio. Phys. vol. 58 (3): 932-940, 2004.
Notification of the Transmittal of the International Search Report and the Written Opinion of the International Searching Authority, or the Declaration, (form ISA/220), International Application No. PCT/GB2016/052575, mailed Nov. 9, 2016 (13 pages).
Notification of the Transmittal of the International Search Report and the Written Opinion of the International Searching Authority, or the Declaration, (form ISA/220), International Application No. PCT/GB2016/052577, mailed Nov. 9, 2016 (10 pages).
Notification of the Transmittal of the International Search Report and the Written Opinion of the International Searching Authority, or the Declaration, (form ISA/220), International Application No. PCT/GB2016/052578, mailed Oct. 25, 2016 (12 pages).
Notification of the Transmittal of the International Search Report and the Written Opinion of the International Searching Authority, or the Declaration, (form ISA/220), International Application No. PCT/GB2016/052581, mailed Oct. 24, 2016 (13 pages).
Schröder E et al., 'Arzneimittel Chemie Passage,' *Arzneimittelchemie Grundlagen Nerven, Muskeln and Gewebe [Pharmaceutical Chemistry I: Basic, Nerves, Muscles and Tissues]*, (1st Ed, 1976), Thieme Georg Verla, Stuttgart DE (Publ) pp. 30-33 and Table 8 XP002186820.
Somei et al., "Boronation-Thallation, A New Approach to the Synthesis of Indoles Having Aryl and/or a Heteroaryl Substituent at the 4-Position." Chem. Pharm. Bull. 1986, 34, 3971-3.
Tao J et al., (2013), 'Combined Treatment of BTK and PI3K Inhibitors Synergistically Disrupts BCR-Signaling, Overcomes Microenvironment-Mediated Survival and Drug Resistance in Mantle Cell Lymphoma,' Proceedings of the 104th Annual Meeting of the American Association for Cancer Research, Apr. 6-10, 2013, Washington, D.C. Philadelphia PA, AACR Abstract #4944, OASIS, Chicago, IL (Publ) (2 pages) [retrieved on Jul. 16, 2014 at <http://wwwabstractsonline.com/Plan/ViewAbstract.aspx?Key=605> . . . ] (Abstract).
Verheijen et al., "Phosphatidylinositol 3-kinase (PI3K) inhibitors as anticancer drugs", Drugs of the Future, 2007, vol. 32, No. 6, pp. 537-547.
Annex to Form PCT/ISA/206 Communication relating to the results of the partial international search for International Application No. PCT/GB2016/052571 mailed Nov. 9, 2016 (4 pages).
Yamada T et al., (2013) 'A Novel HDAC Inhibitor OBP-801 and a PI3K Inhibitor LY294002 Synergistically Induce Apoptosis via the Suppression of Survivin and XIAP in Renal Cell Carcinoma,' Int J Oncol, 43(4)1080-6.
Zhong H et al., (2013) 'Synergistic Effects of Concurrent Blockade of PI3K and MEK Pathways in Pancreatic Cancer Preclinical Models,' PLoS One, 8(10):e77243.

\* cited by examiner

PHOSPHOINOSITIDE 3-KINASE INHIBITORS

CROSS REFERENCE TO RELATED APPLICATIONS

This application is a National Stage Application of International Application Number PCT/GB2013/050583, filed Mar. 8, 2013; which claims priority to Great Britain Application No. 1204125.7, filed Mar. 8, 2012.

FIELD OF THE INVENTION

The present invention relates to novel compounds which act as inhibitors of the class IA phosphoinositide 3-kinase enzyme, PI3K-p110δ, for the treatment of cancer, immune and inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P₃), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110δ activity have important therapeutic potential in cancer and immune and inflammatory disorders.

SUMMARY OF THE INVENTION

The present invention is a compound of formula I:

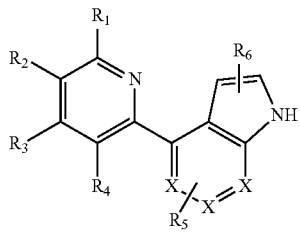

or a pharmaceutically acceptable salt thereof,
wherein:
$R_1$, $R_2$, $R_3$, $R_5$ and $R_6$ are each independently $(LQ)_mY$;
each L is independently a direct bond, $C_1$-$C_{10}$ alkylene, $C_2$-$C_{10}$ alkenylene, $C_2$-$C_{10}$ alkynylene, arylene or $C_3$-$C_{10}$ cycloalkylene;

each Q is independently a direct bond, heteroarylene, a heterocycle linker, —O—, —NR₇—, —OC(O)—, —C(O)NR₇—, —SO₂—, —SO₂—NR₇—, —NR₇—C(O)—NR₇—, —N—SO₂—NR₇—, —C(halogen)$_a$(R$_{7(2-a)}$)—, —NR₈R₉—, —C(O)NR₈R₉—, where R₈ and R₉ together with the nitrogen to which they are attached form a 5 to 7-membered heterocycle linker;
each R₇ is independently H or $C_1$-$C_6$ alkyl;
m is from 0 to 5;
Y is H, $C_1$-$C_{10}$ alkyl, $C_2$-$C_{10}$ alkenyl, $C_2$-$C_{10}$ alkynyl, aryl, $C_3$-$C_{10}$ cycloalkyl, heterocycle, heteroaryl, —OR₇, —N(R₇)₂, —C(O)R₇, —C(O)OR₇, —C(O)N(R₇)₂, —N(R₇)₂, —SO₂—R₇, —SO₂—N(R₇)₂, —N—C(O)—N(R₇)₂, —N—SO₂—N(R₇)₂, halogen, —C(halogen)$_b$R$_{7(3-b)}$, —CN, —NR₈R₉—, —C(O)NR₈R₉, where R₈ and R₉ together with the nitrogen to which they are attached form a 5- to 7-membered heterocycle;
b is from 1 to 3;
a is 1 or 2;
R₄ is H, halogen, optionally substituted aryl or optionally substituted alkyl; and;
each X is independently CR₇ or N,
wherein each aryl, heteroaryl or heterocycle is optionally substituted with up to three substituents selected from $C_1$-$C_8$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —SO₃H, $C_1$-$C_3$ alkylsulfonyl, aminosulfonyl, mono $C_1$-$C_3$ alkyl aminosulfonyl and bis $C_1$-$C_3$-alkyl aminosulfonyl.

DESCRIPTION OF PREFERRED EMBODIMENTS

For the avoidance of doubt, the term "$R_1$, $R_2$, $R_3$, $R_5$ and $R_6$ are each independently $(LQ)_mY$" means:
When m is 0, $R_n$ is Y;
When m is 1, $R_n$ is L-Q-Y;
When m is 2, $R_n$ is L-Q-L-Q-Y (and each L and each Q group are the same or different);
When m is 3, $R_n$ is L-Q-L-Q-L-Q-Y (and each L and each Q group are the same or different); etc
Preferably m is 0 or 1.
As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent, e.g. propylene. In general, the suffix "-ene" means that the group is divalent.
As used herein, "cycloalkyl" contains from 3 to 10 carbon atoms. It may be monovalent or divalent.
As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent, e.g. propenylene
As used herein, "alkynyl" is a $C_2$-$C_{10}$ alkynyl group which can be linear or branched. Preferably, it is a $C_2$-$C_4$ alkynyl group or moiety. It may be divalent.
Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with any of the "optional substituents" defined below.

As used herein, "aryl" means a monocyclic, bicyclic, or tricyclic monovalent or divalent aromatic radical, such as phenyl, biphenyl, naphthyl, anthracenyl, which can be optionally substituted with up to five substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent aromatic radical containing up to four heteroatoms selected from oxygen, nitrogen and sulfur, such as thiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heterocycle" is a mono- or di-valent non-aromatic carbocyclic radical containing up to 4 heteroatoms selected from oxygen, nitrogen and sulfur. The word 'linker' has been used herein to mean di-valent. If the heterocycle is a di-valent linker, the heterocycle may be attached to neighbouring groups through a carbon atom, or through one of the heteroatoms, e.g. a N.

The above groups can be followed by the suffix -ene. This means that the group is divalent, i.e. a linker group.

As used herein, "optionally substituted" preferably means optionally substituted with up to three "optional substituents" selected from $C_1$-$C_8$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo e.g. F, Cl, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In $R_4$, preferably halogen is fluorine.

Preferably, $R_1$ is an optionally substituted aryl or optionally substituted heterocycle, preferably a nitrogen-containing one. More preferably, $R_1$ is morpholinyl, piperidinyl, piperazinyl, pyrrolidinyl, cyclohexylamino, cyclopentylamino, piperidin-4-yl, N-acetylpiperazinyl, thiomorpholinyl, thiomorpholinyldioxide, 4-hydroxyethylpiperidinyl, and 4-hydroxypiperidinyl. Still more preferably, $R_1$ is represented by any of the following structures:

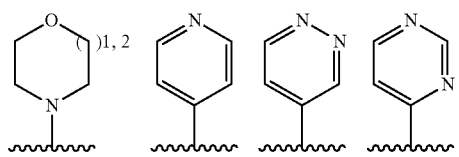

Most preferably, $R_1$ is morpholino.

Preferably, $R_2$ is $C_1$-$C_6$ alkyl, H, halogen or C(halogen)$_b$R$_{7(3-b)}$, where b is from 1 to 3. More preferably $R_2$ is $C_1$-$C_6$ alkyl or H. More preferably $R_2$ is H.

In a preferred embodiment at least one X is CH. Preferably, each X is CH.

Preferably, $R_2$ is H.

Preferably, $R_4$ is H.

Preferably, $R_5$ and/or $R_6$ is H. More preferably, $R_5$ and $R_6$ are H.

Preferably, $R_3$ is $NR_7R_7$.

Preferably, $R_3$ is $NR_7C(O)(C_1$-$C_{10}$ alkylene)$NR_8R_9$.

Preferably, $R_3$ is $NR_7C(O)(C_1$-$C_{10}$ alkylene)$NR_7R_7$.

In a preferred embodiment, a compound of the invention is as exemplified herein, i.e. compound A, B or C.

For the avoidance of doubt, a moiety designated as, for example, —C(O)NR$_7$—, is not direction specific, it can also be positioned as —NR$_7$—C(O)—.

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by co-administration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Oster Webber syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other than the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative tumours including PTEN-negative haematological, breast, lung, endometrial, skin, brain and prostrate cancers (where PTEN refers to "phosphatise and tensin homolog deleted on chromosome 10"). More preferably, the condition to be treated by a compound of the invention is rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. More preferably, The invention will now be illustrated by the following Examples.

EXAMPLES

A. 2-(1H-Indol-4-yl)-6-morpholin-4-yl-pyridin-4-ylamine, 2

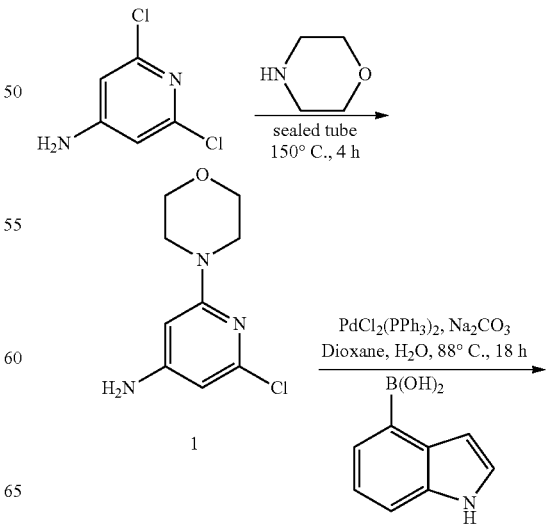

-continued

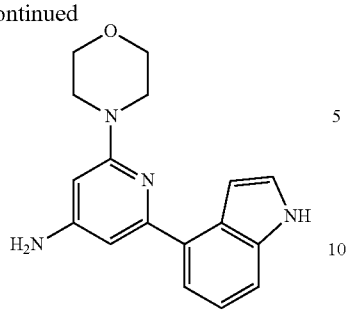

A

-continued

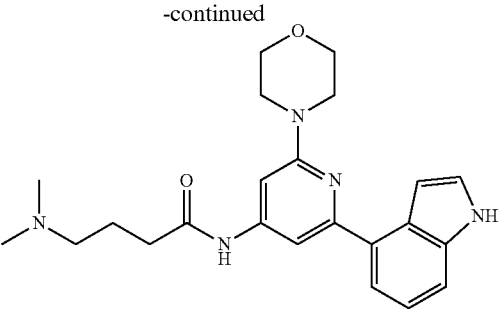

B i) Synthesis of 2-chloro-6-morpholin-4-yl-pyridin-4-ylamine, 1

A sealed tube charged with 2,6-dichloro-pyridin-4-ylamine (500 mg, 3.1 mmol, 1 eq) and morpholine (2.3 mL, 26.3 mmol, 9 eq) was heated up to 150° C. for 4 h. Once cooled down, the reaction mixture was partitioned with H$_2$O (10 mL) and extracted with EtOAc (3×20 mL). The combined organic extracts were washed with H$_2$O (2×5 mL), dried over MgSO$_4$, and the solvent was removed in vacuo. The resulting residue was further purified by silica gel column chromatography with hexane/EtOAc (1:1-2:3) to furnish 1 as a pink solid (555 mg, 85%).

$^1$H NMR (400 MHz, DMSO-d$_5$) δ$_H$ ppm: 6.03 (s, 2H), 5.95 (d, J=1.4 Hz, 1H), 5.75 (d, J=1.4 Hz, 1H), 3.62-3.67 (m, 4H), 3.23-3.28 (m, 4H); MS (ES$^+$) 214.1 (100%, [M+H]$^+$).

ii) Synthesis of 2-(1H-indol-4-yl)-6-morpholin-4-yl-pyridin-4-ylamine, A

To a flask charged with indole-4-boronic acid (791 mg, 4.91 mmol, 3 eq), dichloro-bis(triphenylphosphine)palladium (II) (230 mg, 0.33 mmol, 0.2 eq) and sodium carbonate (348 mg, 3.28 mmol, 2 eq), was added compound 1 (350 mg, 1.64 mmol, 1 eq) dissolved in dioxane/water (40 mL, 3:1). The resulting reaction mixture was then heated at 88° C. for 18 h under Ar(g); once cooled down, it was then partitioned with H$_2$O (20 mL) and extracted with EtOAc (4×20 mL) and CH$_2$Cl$_2$ (15 mL). The combined organic extracts were dried over MgSO$_4$ and the solvent was then removed in vacuo. The residue was further purified by silica gel column chromatography, eluting with hexane/EtOAc (1:1-0:1), to yield the product as a white solid (273 mg, 56%).

$^1$H NMR (400 MHz, DMSO-d$_5$) δ$_H$ ppm: 11.12 (br. s, 1H), 7.39 (s, 1H), 7.35-7.38 (m, 2H), 7.12 (s, 1H), 6.87 (br. s., 1H), 6.56 (s, 1H), 5.85-5.88 (m, 1H), 5.74 (br. s., 2H), 3.68-3.74 (m, 4H), 3.37-3.42 (m, 4H); MS (ES$^+$) 295.0 (100%, [M+H]$^+$).

B. 4-Dimethylamino-N-[2-(1H-indol-4-yl)-6-morpholin-4-yl-pyridin-4-yl]-butyramide

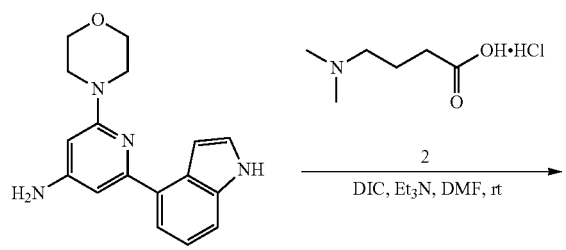

1

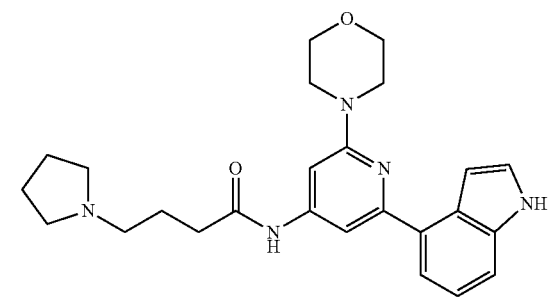

To a solution of 4-dimethylamino-butyric acid hydrochloride, 2 (29 mg, 0.17 mmol, 2 eq) and DIC (26 μL, 0.17 mmol, 2 eq) in DMF (1 mL) was added Et$_3$N (48 mL, 0.34 mmol, 4 eq) at rt. After 30 min, amine 1 (25 mg, 0.085 mmol, 1 eq) was dissolved in DMF (1 mL) and was added to the reaction mixture, which was then heated at 60° C. for 4 h. Once cooled down, the reaction mixture was partitioned with NaHCO$_3$ (10 mL) and extracted with EtOAc (3×10 mL). The combined organic extracts were dried over MgSO$_4$ and the solvent was removed in vacuo. The resulting residue was further purified by silica gel column chromatography with CH$_2$Cl$_2$/MeOH (1:0-9:1+0.3M NH$_3$) to furnish the product as a white solid (26 mg, 74%).

$^1$H NMR (400 MHz, CDCl$_3$) δ$_H$ ppm: 10.44 (br. s, 1H), 8.28 (br. s, 1H), 7.54 (d, J=7.4 Hz, 1H), 7.43 (d, J=8.1 Hz, 1H), 7.37 (s, 1H), 7.24-7.30 (m, 2H), 7.07-7.10 (m, 1H), 7.00 (d, J=0.9 Hz, 1H), 3.83-3.88 (m, 4H), 3.63-3.68 (m, 4H), 2.53-2.59 (m, 2H), 2.51 (t, J=5.9 Hz, 2H), 2.36 (s, 6H), 1.90 (quin, J=6.1 Hz, 2H); MS (ES$^+$) 408.0 (100%, [M+H]$^+$).

C. N-[2-(1H-Indol-4-yl)-6-morpholin-4-yl-pyridin-4-yl]-4-pyrrolidin-1-yl-butyramide

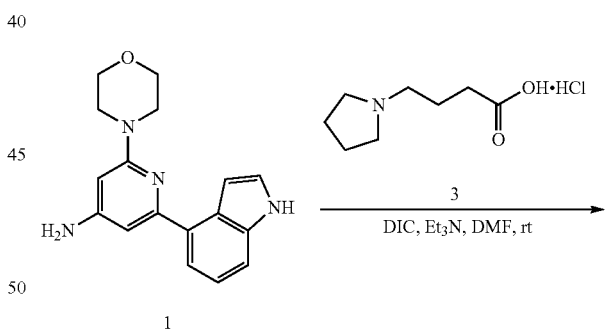

1

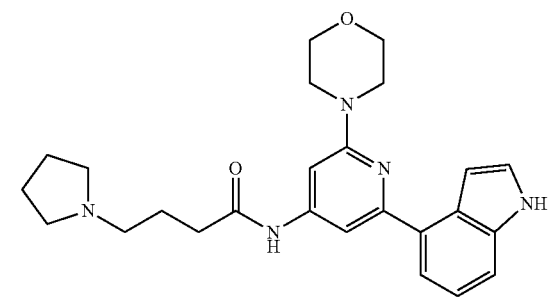

C

To a solution of 4-pyrrolidin-1-yl-butyric acid hydrochloride, 3, (33 mg, 0.17 mmol, 2 eq) and DIC (26 μL, 0.17 mmol, 2 eq) in DMF (1 mL) was added Et$_3$N (47 mL, 0.34 mmol, 4 eq) at rt. After 30 min, the amine 1 (25 mg, 0.085 mmol, 1 eq) was dissolved in DMF (1 mL) and added to the reaction mixture, which was then heated at 60° C. for 4 h. Once cooled, the reaction mixture was partitioned with NaHCO$_3$ (10 mL) and extracted with EtOAc (3×10 mL) and CH$_2$Cl$_2$ (10 mL). The combined organic extracts were dried over MgSO$_4$ and the solvent was removed in vacuo. The resulting residue was further purified by silica gel column chromatography, eluting with CH$_2$Cl$_2$:MeOH (1:0-6:1+ 0.3M NH$_3$) to furnish the product as a white solid (4.5 mg, 12%).

$^1$H NMR (400 MHz, CDCl$_3$) δ$_H$ ppm: 7.48 (d, J=7.3 Hz, 1H), 7.41 (d, J=8.1 Hz, 1H), 7.32 (s, 1H), 7.25 (m, J=3.0 Hz, 1H), 7.18 (t, J=7.7 Hz, 1H), 7.12 (s, 1H), 6.95-6.98 (m, 1H), 3.79-3.85 (m, 4H), 3.58 (t, J=4.6 Hz, 4H), 3.26-3.36 (m, 2H), 3.08-3.13 (m, 1H), 3.01 (t, J=7.5 Hz, 2H), 2.54 (t, J=7.0 Hz, 2H), 2.46 (t, J=6.7 Hz, 1H), 1.93-2.08 (m, 4H), 1.16 (t, J=7.1 Hz, 1H), 1.08 (t, J=7.2 Hz, 1H), MS (ES$^+$) 434.0 (100%, [M+H]$^+$).

The following biochemical data have been generated for the exemplified compounds, showing PI3K binding potency.

Biochemical Data

| Compound | IC$_{50}$ (nM), PI3K-p110α | IC$_{50}$ (nM), PI3K-p110β | IC$_{50}$ (nM), PI3K-p110δ | IC$_{50}$ (nM), PI3K-p110γ |
|---|---|---|---|---|
| B | ≥10,000 | 247 | 177 | ≥10,000 |
| C |  |  | 953 |  |

The invention claimed is:

1. A compound of formula I:

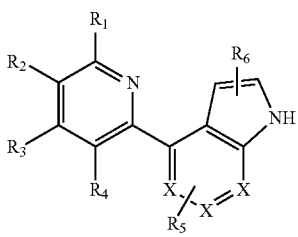

or a pharmaceutically acceptable salt thereof, wherein:
R$_1$ is morpholino;
R$_2$, R$_3$, R$_5$ and R$_6$ are each independently (LQ)$_m$Y;
each L is independently selected from the group consisting of a direct bond, C$_1$-C$_{10}$ alkylene, C$_2$-C$_{10}$ alkenylene, C$_2$-C$_{10}$ alkynylene, arylene and C$_3$-C$_{10}$ cycloalkylene;
each Q is independently selected from the group consisting of a direct bond, heteroarylene, a heterocycle linker, —O—, —NR$_7$—, —C(O)—, —C(O)NR$_7$—, —SO$_2$—, —SO$_2$—NR$_7$—, —NR$_7$—C(O)—NR$_7$—, —N—SO$_2$—NR$_7$—, —C(halogen)$_a$(R$_{7(2a)}$)—, —NR$_8$R$_9$—, and —C(O)NR$_8$R$_9$—, where R$_8$ and R$_9$ together with the nitrogen to which they are attached form a 5 to 7-membered heterocycle linker;
each R$_7$ is independently H or C$_1$-C$_6$ alkyl;
m is from 0 to 5;
Y is selected from the group consisting of H, C$_1$-C$_{10}$ alkyl, C$_2$-C$_{10}$ alkenyl, C$_2$-C$_{10}$ alkynyl, aryl, C$_3$-C$_{10}$ cycloalkyl, heterocycle, heteroaryl, —OR$_7$, —N(R$_7$)$_2$, —C(O)R$_7$, —C(O)OR$_7$, —C(O)N(R$_7$)$_2$, —N(R$_7$)$_2$, —SO$_2$—R$_7$, —SO$_2$—N(R$_7$)$_2$, —N—C(O)—N(R$_7$)$_2$, —N—SO$_2$—N(R$_7$)$_2$, halogen, —C(halogen)$_b$R$_{7(3-b)}$, —CN, —NR$_8$R$_9$—, and —C(O)NR$_8$R$_9$, where R$_8$ and R$_9$ together with the nitrogen to which they are attached form a 5- to 7-membered heterocycle; b is from 1 to 3;
a is 1 or 2;
R$_4$ is selected from the group consisting of H, halogen, optionally substituted aryl and optionally substituted alkyl; and
each X is independently CR$_7$ or N;
wherein each aryl, heteroaryl or heterocycle is optionally substituted with up to three substituents, each of which is selected from the group consisting of C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis (C$_1$-C$_3$ alkyl) amino C$_1$-C$_3$ alkyl, C$_1$-C$_3$-acylamino, C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl and bis C$_1$-C$_3$-alkyl aminosulfonyl.

2. The compound according to claim 1, wherein R$_2$ is H.

3. The compound according to claim 1, wherein R$_4$ is H.

4. The compound according to claim 1, wherein each X is CH.

5. The compound according to claim 1, wherein R$_5$ and/or R$_6$ is H.

6. The compound according to claim 1, wherein R$_3$ is NR$_7$C(O)(C$_1$-C$_{10}$ alkylene)NR$_7$R$_7$.

7. The compound according to claim 1, which is selected from the group consisting of:
2-(1H-indol-4-yl)-6-morpholin-4-yl-pyridin-4-ylamine;
4-dimethylamino-N-[2-(1H-indol-4-yl)-6-morpholin-4-yl-pyridin-4-yl]-butyramide; and
N-[2-(1H-indol-4-yl)-6-morpholin-4-yl-pyridin-4-yl]-4-pyrrolidin-1-yl-butyramide.

8. A pharmaceutical composition comprising the compound according to claim 1, and a pharmaceutically acceptable excipient.

9. A compound of formula I:

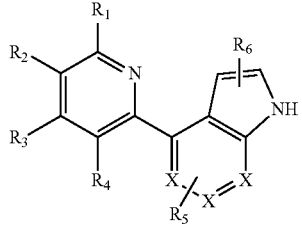

or a pharmaceutically acceptable salt thereof, wherein:
R$_1$R$_2$, R$_5$ and R$_6$ are each independently (LQ)$_m$Y;
each L is independently selected from the group consisting of a direct bond, C$_1$-C$_{10}$ alkylene, C$_2$-C$_{10}$ alkenylene, C$_2$-C$_{10}$ alkynylene, arylene and C$_3$-C$_{10}$ cycloalkylene;
each Q is independently selected from the group consisting of a direct bond, heteroarylene, a heterocycle linker, —O—, —NR$_7$—, —C(O)—, —C(O)NR$_7$—, —SO$_2$—, —SO$_2$—NR$_7$—, —NR$_7$—C(O)—NR$_7$—, —N—SO$_2$—NR$_7$—, —C(halogen)$_a$(R$_{7(2-a)}$)—, —NR$_8$R$_9$—, and —C(O)NR$_8$R$_9$—, where R$_8$ and R$_9$ together with the nitrogen to which they are attached form a 5 to 7-membered heterocycle linker;

R$_3$ is NR$_7$C(O)(C$_1$-C$_{10}$ alkylene)NR$_7$R$_7$;

each R$_7$ is independently H or C$_1$-C$_6$ alkyl;

m is from 0 to 5;

Y is selected from the group consisting of H, C$_1$-C$_{10}$ alkyl, C$_2$-C$_{10}$ alkenyl, C$_2$-C$_{10}$ alkynyl, aryl, C$_3$-C$_{10}$ cycloalkyl, heterocycle, heteroaryl, —OR$_7$, —N(R$_7$)$_2$, —C(O)R$_7$, —C(O)OR$_7$, —C(O)N(R$_7$)$_2$, —N(R$_7$)$_2$, —SO$_2$—R$_7$, —SO$_2$—N(R$_7$)$_2$, —N—C(O)—N(R$_7$)$_2$, —N—SO$_2$—N(R$_7$)$_2$, halogen, —C(halogen)$_b$R$_{7(3-b)}$, —CN, —NR$_8$R$_9$—, and —C(O)NR$_8$R$_9$, where R$_8$ and R$_9$ together with the nitrogen to which they are attached form a 5- to 7-membered heterocycle; b is from 1 to 3;

a is 1 or 2;

R$_4$ is selected from the group consisting of H, halogen, optionally substituted aryl and optionally substituted alkyl; and each X is independently CR$_7$ or N;

wherein each aryl, heteroaryl or heterocycle is optionally substituted with up to three substituents, each of which is selected from the group consisting of C$_1$-C$_6$ alkyl, hydroxy, C$_1$-C$_3$ hydroxyalkyl, C$_1$-C$_3$ alkoxy, C$_1$-C$_3$ haloalkoxy, amino, C$_1$-C$_3$ mono alkylamino, C$_1$-C$_3$ bis alkylamino, C$_1$-C$_3$ acylamino, C$_1$-C$_3$ aminoalkyl, mono (C$_1$-C$_3$ alkyl) amino C$_1$-C$_3$ alkyl, bis (C$_1$-C$_3$ alkyl) amino C$_1$-C$_3$ alkyl, C$_1$-C$_3$-acylamino, C$_1$-C$_3$ alkyl sulfonylamino, halo, nitro, cyano, trifluoromethyl, carboxy, C$_1$-C$_3$ alkoxycarbonyl, aminocarbonyl, mono C$_1$-C$_3$ alkyl aminocarbonyl, bis C$_1$-C$_3$ alkyl aminocarbonyl, —SO$_3$H, C$_1$-C$_3$ alkylsulfonyl, aminosulfonyl, mono C$_1$-C$_3$ alkyl aminosulfonyl and bis C$_1$-C$_3$-alkyl aminosulfonyl.

10. The compound according to claim 9, wherein R$_1$ is optionally substituted heteroaryl or heterocycle, wherein the optional substituents are as defined in claim 1.

11. The compound according to claim 9, wherein R$_2$ is H.

12. The compound according to claim 9, wherein R$_4$ is H.

13. The compound according to claim 9, wherein each X is CH.

14. The compound according to claim 9, wherein R$_5$ and/or R$_6$ is H.

15. A pharmaceutical composition comprising the compound according to claim 9, and a pharmaceutically acceptable excipient.

* * * * *